(12) United States Patent
Lindquist (10) Patent No.: US 12,082,952 B2
(45) Date of Patent: Sep. 10, 2024

(54) CURVED COUCH TOPS FOR O-RING TREATMENT UNITS

(71) Applicant: Varian Medical Systems, Inc., Palo Alto, CA (US)

(72) Inventor: Eric Lindquist, Menlo Park, CA (US)

(73) Assignee: Varian Medical Systems, Inc, Palo Alto, CA (US)

( * ) Notice: Subject to any disclaimer, the term of this patent is extended or adjusted under 35 U.S.C. 154(b) by 644 days.

(21) Appl. No.: 17/359,288

(22) Filed: Jun. 25, 2021

(65) Prior Publication Data
US 2022/0409150 A1    Dec. 29, 2022

(51) Int. Cl.
*A61B 6/00* (2024.01)
*A61B 6/04* (2006.01)
*A61N 5/10* (2006.01)

(52) U.S. Cl.
CPC ........ *A61B 6/0407* (2013.01); *A61N 5/1081* (2013.01)

(58) Field of Classification Search
CPC .................................................... A61B 6/0407
See application file for complete search history.

(56) References Cited

U.S. PATENT DOCUMENTS

2021/0378607 A1\* 12/2021 Chae ................... A61B 6/04

\* cited by examiner

*Primary Examiner* — Dani Fox
(74) *Attorney, Agent, or Firm* — Harness, Dickey & Pierce, P.L.C.

(57) ABSTRACT

A radiation system employs a couch top rotatable about a yaw axis to provide non-coplanar irradiation of a patient in an O-ring type of radiation machine. The radiation machine includes a source operable to produce radiation and a housing enclosing the source. The housing defines a bore and the source is rotatable at least partially around the bore. The couch top is adapted to be rotatable about a yaw axis, thereby allowing non-coplanar irradiation of at least a portion of the patient by the source. A radiation method is also provided.

19 Claims, 6 Drawing Sheets

CURVED COUCH TOPS FOR O-RING TREATMENT UNITS

TECHNICAL FIELD

This application relates generally to radiation treatment and imaging. In particular, various embodiments of a couch top supporting patients for radiation treatment and/or imaging are described.

BACKGROUND

Radiation machines are used in a variety of applications including treatment and imaging of patients. One type of radiation machine employs a rotatable gantry in the shape of a C-arm on which a source of radiation is mounted in a cantilevered manner. The source of radiation rotates with the C-arm gantry about an axis e.g., a horizontal axis passing through an isocenter, allowing for delivery of radiation to a treatment volume in a patient from multiple angles. Another type of radiation machine includes a stationary gantry or housing in the shape of a toroid or O-ring, which defines a central opening or bore for receiving a patient or a portion of a patient. A source of radiation within the housing rotates around the bore, allowing for delivery of radiation to a treatment volume in a patient from multiple angles.

Radiation machines with a rotatable C-arm gantry provide greater flexibility of access of radiation to the treatment volume, allowing for implementation of non-coplanar treatments through the use of a combination of different gantry rotation angles and patient table maneuvers. One problem with conventional C-arm systems is that, due to their open geometry, collision avoidance can be very complicated. More elaborate room shielding may be required to block radiation not intercepted by the C-arm machine itself. Conversely, O-ring type of radiation machines do not require complicated collision avoidance mechanisms, can provide efficient treatment by using a series of rapid cartesian movements of the source, and are more conducive to self-shielding. However, one major limitation of conventional O-ring systems is that they generally do not allow for non-coplanar treatments.

Therefore, there exists a need for solving the problems or limitations of conventional radiation systems discussed above. It would be desirable to provide a radiation system that allows for efficient treatment and flexibility of non-coplanar treatment. It would be desirable to provide an O-ring type of radiation system with a capability of treating non-coplanar indications to expand the performance of the radiation system and treatment outcomes for the patient.

SUMMARY

An embodiment of the disclosure provides a radiation system comprising a radiation machine and a supporting device. The radiation machine comprises a source operable to produce radiation and a housing enclosing the source. The housing defines a bore and the source is rotatable at least partially around the bore. The supporting device comprises a couch and a couch top configured to position at least a portion of a patient in the bore. The couch top is rotatable about a yaw axis thereby allowing for non-coplanar irradiation of at least the portion of the patient by the source.

An embodiment of the disclosure provides a radiation method comprising the following steps. A couch top supporting a patient is positioned in a first irradiation position in a radiation machine which comprises a source of radiation in a housing having a bore. The source of radiation is rotatable at least partially around the bore about a rotation axis. In the first irradiation position, the longitudinal axis of the couch top forms a first angle with respect to the rotation axis of the source of radiation. In the first irradiation position, radiation from the source is delivered to at least a portion of the patient supported on the couch top. Then the couch top supporting the patient is positioned in a second irradiation position in the radiation machine. In the second irradiation position, the longitudinal axis of the couch top forms a second angle with respect to the rotation axis of the source of radiation. In the second irradiation position, radiation from the source is delivered to at least the portion of the patient supported on the couch top.

This Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings provided below, where:

FIGS. 2A-2C depict an example of a radiation system according to the disclosure.

DETAILED DESCRIPTION OF EMBODIMENTS

With reference to FIGS. 1-4, various embodiments of a radiation system and a radiation method will now be described. It should be noted that the figures are intended for illustration of embodiments but not for exhaustive description or limitation on the scope of the disclosure. Alternative structures and method steps will be readily recognized as being viable without departing from the principle of the claimed invention.

In general, the disclosure provides solutions to the need for efficient treatment with a flexibility of non-coplanar treatment. One solution is to employ a contoured couch top that allows for extended yaw movements in an O-ring treatment unit. The yaw movements of the couch top change the angle of the longitudinal axis of the couch top and thus the superior-inferior direction of the patient supported thereon with respect to the rotation axis of the source of radiation, thereby allowing for non-coplanar irradiation of the patient in the O-ring treatment unit.

Figure 1:
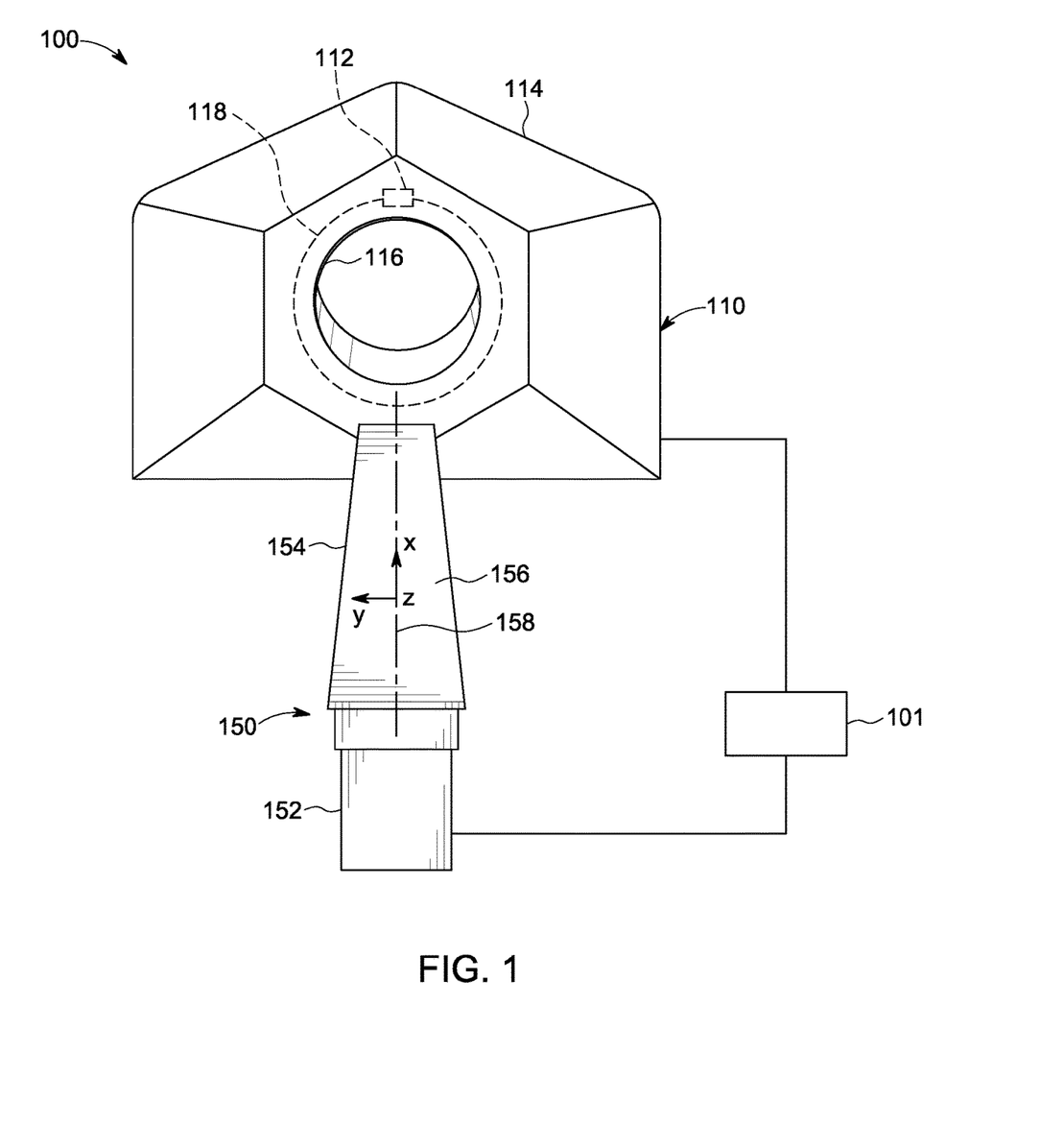
FIG. 1 is a simplified illustration of a radiation system according to embodiments of the disclosure.

FIG. 1 depicts an example of a radiation system 100 according to embodiments of the disclosure. As shown, the radiation system 100 includes a radiation machine 110 and a supporting device 150. The operation of the radiation machine 110 and the supporting device 150 can be controlled by a computer control 101. The radiation machine 110 may include a source of radiation 112 operable to produce or emit e.g., x-rays, electrons, protons or heavy ions, or other types of radiation. The source 112 may be operated at a high energy level such as a megavolt level to produce radiation suitable for therapeutic treatment. It should be noted that while embodiments of the disclosure are described in conjunction with a treatment system, the principle of the disclosure can be applied in an imaging system such as a system of computed tomography (CT), cone beam computed tomography (CBCT), spiral CT, sliding CT, position-emission tomography (PET), fluoroscopy, radiography, ultrasound imaging, magnetic resonance imaging (MRI), etc.

With reference to FIG. 1, the radiation machine 110 may include a gantry or housing 114. The gantry or housing 114 may be stationary e.g., directly or indirectly fixed to the floor in a treatment room. Alternatively, the gantry 114 is capable of rotating. The housing 114 may be in the form or shape defining an opening or a bore 116 configured, e.g., sized and shaped, to allow a patient or a portion of a patient to be positioned in the bore for receiving radiation. The source of radiation 112 within the housing 114 is rotatable at least partially around the bore 116, allowing irradiation of the patient or a portion of the patient from multiple angles. In an embodiment, the source of radiation 112 within the housing 114 is rotatable around the bore 116 in 360 degrees or more. By way of example, the source of radiation 112 may ride or move on a ring structure 118 within the housing 114, which provides for an orbit for the source 112 to rotate around the bore 116. The ring structure 118 may be a closed or full ring structure allowing the source 112 to rotate around the bore 116 in 360 degrees or more. The ring structure 112 may also be an open or partial ring structure allowing the source 112 to rotate at least partially around the bore 116. Other types of the structures providing an orbit of rotation for the source are possible and contemplated by the disclosure.

With reference to FIG. 1, the supporting device 150 may include a couch 152 and a couch top 154. The couch top 154 may have a supporting surface 156 and a longitudinal axis 158. A patient (not shown) may be supported on the couch top 154, either prone, supine, or side way, with the superior-inferior direction of the patient being generally in line with the longitudinal axis 158 of the couch top 154. The patient supported on the couch top 154 may be immobilized with various immobilization devices (not shown).

With reference to FIG. 1, the couch 152 may be fixed to the floor in a treatment room. Alternative, the couch 152 may be movable horizontally by a motion axis to allow the couch top 154 and thus the patient supported thereon to extend into the bore 116 of the radiation machine 110. The couch 152 may also be movable vertically by a motion axis to allow the height of the couch top 154 and thus the patient supported thereon to be adjusted. In some embodiments, the couch 152 may be rotated by one or more motion axes, thereby allowing the couch top 154 and thus the patient supported thereon to roll, pitch, or yaw respectively.

With reference to FIG. 1, according to embodiments of the disclosure, instead of or in addition to moving the couch 152, the couch top 154 may be individually movable, independent of the couch 152. For example, the supporting device 150 may include one or more motion axes configured to move the couch top 154 and thus the patient supported thereon, horizontally and/or vertically, thereby allowing the patient or a portion of the patient to be extended into the bore 116 and positioned relative to the source of radiation 112.

The supporting device 150 may also include one or more motion axes configured to rotate, e.g., to roll, pitch, or yaw the couch top 154 and thus the patient supported thereon.

To facilitate description of various embodiments, the term "roll axis" is used herein to refer to an axis that is parallel with both the longitudinal axis 158 and the supporting surface 156 of the couch top 154 (e.g., x-axis as indicated in FIG. 1). A rotation of the couch top 154 about the roll axis (e.g., x-axis), or a roll rotation, may cause the patient or a portion of the patient to roll or turn clockwise or counterclockwise. The term "pitch axis" is used herein to refer to an axis that is perpendicular to the longitudinal axis 158 and parallel with the supporting surface 156 of the couch top 154 (e.g., y-axis as indicated in FIG. 1). A rotation of the couch top 154 about the pitch axis (e.g., y-axis), or a pitch rotation, may cause the patient or a portion of the patient in the bore to move up or down relative to the source 112. The term "yaw axis" is used herein to refer to an axis that is perpendicular to both the longitudinal axis 158 and the supporting surface 156 of the couch top 154 (e.g., z-axis perpendicular to the x-y plane as indicated in FIG. 1). A rotation of the couch top about the yaw axis (e.g., z-axis), or a yaw rotation, may cause the patient or a portion of the patient in the bore to move from side to side. According to embodiments of the disclosure, the couch top 154 is adapted to be rotatable at least about a yaw axis, thereby allowing for non-coplanar irradiation of the patient or a portion of the patient by the source of radiation 112, as will be described further below. According to embodiments of the disclosure, the couch top 154 is further adapted to be rotatable about a roll axis, allowing rolling of the couch top 154 and thus the patient supported thereon clockwise or counterclockwise, and/or further adapted to be rotatable about a pitch axis, allowing lowering or raising the front end of the couch top 154 and thus the patient supported thereon. The capability of a yaw rotation, optionally in combination with a roll rotation and/or a pitch rotation of the couch top 154, provides greater flexibility in achieving non-coplanar irradiation of a patient in an O-ring radiation system.

Figure 2A:
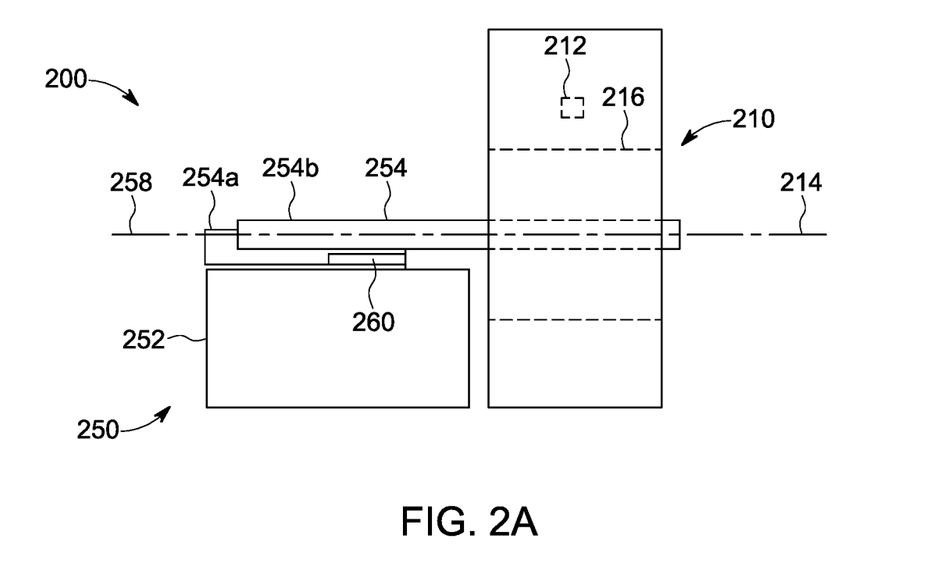
FIG. 2A is a side view of the radiation system.
Figure 2B:
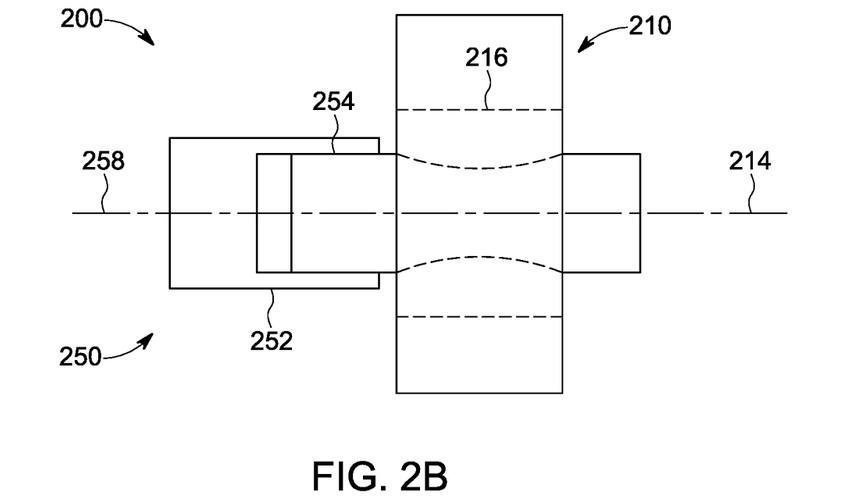
FIGS. 2B-2C are top views of the radiation system.
Figure 2C:
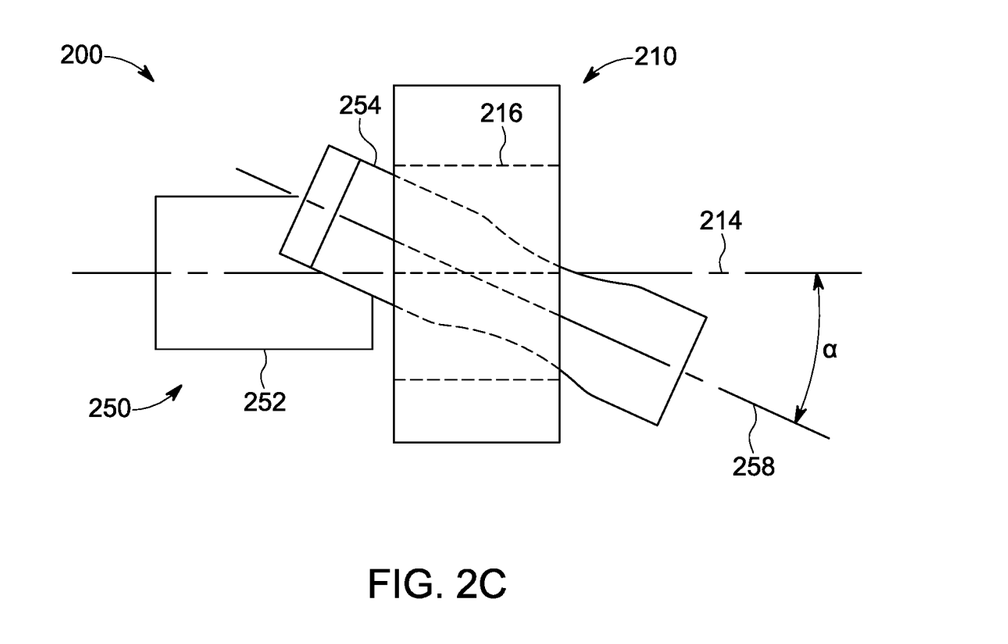

FIGS. 2A to 2C depict an example of a radiation system 200 according to embodiments of the disclosure. FIG. 2A is a side view of the radiation system 200. FIGS. 2B and 2C are top views of the radiation system 200. As shown, the radiation system 200 may include a radiation machine 210 and a supporting device 250. The radiation machine 210 may be the same as or similar to the radiation machine 110 described above in conjunction with FIG. 1. The radiation machine 210 may include a source of radiation 212 rotatable about a rotation axis, e.g., a horizontal axis 214 perpendicular to a cross-section of the bore 216 of the radiation machine 210, as indicated in FIG. 2A. The supporting device 250 may include a couch 252 and a couch top 254. The couch top 254 may be extended into the bore 216 and placed in a first irradiation position as shown in FIG. 2B, where, for example, the longitudinal axis 258 of the couch top 254, and thus the superior-inferior direction of the patient supported thereon, aligns with the rotation axis 214 of the radiation machine 210. In the first irradiation position shown in FIG. 2B, the patient or a portion of the patient, may receive radiation from multiple angles, or receive radiation from the source 212 at multiple angles while the source 212 rotates around the bore 216 of the radiation machine 210. The couch top 254 may be rotated about a yaw axis and placed in a second irradiation position as shown in FIG. 2C, where, for example, the longitudinal axis 258 of the couch top 254, and thus the superior-inferior direction of the patient supported thereon, forms a non-zero angle (a) with respect to the rotation axis 214 of the source of radiation 212. In the second irradiation position shown in FIG. 2C, the patient or a portion of the patient, may receive radiation from multiple angles, or receive radiation from the source 212 at multiple angles while the source 212 rotates around the bore 216 of the radiation machine 210. Therefore, although the source of radiation 212 may be constrained in a coplanar plane while rotating around the bore 216 of the radiation machine 210, because the couch top 254 is rotatable about a yaw axis allowing the angle of the longitudinal axis 258 of the couch top 254 and thus the superior-inferior direction of the patient supported thereon to change with respect to the rotation axis 214 of the source of radiation 212, non-coplanar irradiation of the patient or a portion of the patient can be achieved.

According to embodiments of the disclosure, the couch top 254 is rotatable about a yaw axis in at least about 1-10 degrees, clockwise and/or counterclockwise. According to embodiments of the disclosure, the couch top 254 is rotatable about a yaw axis up to 40-50 degrees, clockwise and/or counterclockwise. Alternatively, according to embodiments of the disclosure, the couch top 254 is rotatable about a yaw axis to allow forming an angle ranging from about 1 degree to about 20 degrees, or from about 1 degree to about 25 degrees, between the longitudinal axis 258 of the couch top 254 and the rotation axis 214 of the source of radiation 212. The dimension of the bore 216 of the radiation machine 210, and/or, a portion of the couch top 254, can be contoured and/or sized to accommodate the yaw rotation of the couch top 254, to form a desired angle between the longitudinal axis 258 of the couch top 254 and the rotation axis 214 of the source of radiation 212.

With reference to FIGS. 2A-2C, the supporting device 250 may include a mechanism 260 (FIG. 2A) configured to independently rotate the couch top 254 about a yaw axis, and optionally to further rotate the couch top 254 about a roll axis and/or a pitch axis. Various mechanisms may be used to perform the yaw rotation, optionally the roll and/or pitch rotation. An example of a mechanical mechanism 260 includes a wrist assembly operable to rotate the couch top 254 in three degrees of freedom. By way of example, a wrist assembly 260 may include a first wrist for yaw rotation, a second wrist for roll rotation, and a third wrist for pitch rotation. Optionally, the mechanism 260 may be further moved by one or motion axes to vertically and/or horizontally translate the couch top 254 in three degrees of freedom. Therefore, in an embodiment of the disclosure, the supporting device 250 may include a mechanical mechanism 260 operable to move the couch top 254 in all six degrees of freedom, independent of the couch 252. Another example of a mechanical mechanism 260 includes a movable stage, which can be rotated and/or translated by a combination of lift assemblies and rotatory joints.

With reference to FIGS. 2A-2C, according to embodiments of the disclosure, the couch top 254 may include a single piece or board. Alternatively, the couch top 254 may include multiple pieces or sections. For example, the couch top 254 may include an interface plate e.g., a universal mount 254a and a couch top extension or insert 254b which can be removably attached to the interface plate 254a, as shown in FIG. 2A. The interface plate 254a and the couch top extension 254b may include attachment mechanisms to allow for attaching the couch top extension 254b to and dis-attaching the couch top extension 254b from the interface plate 254a. By way of example, the interface plate 254a and the couch top extension 254b may include complementary hook and bar structures, and/or complementary protrusion and slot structures, or the like, allowing the couch top extension 254b to be removably attached to the interface plate 254a. The use of couch top extensions 254b with an interface plate e.g., a universal couch mount 254a allows for interchanging of couch tops or replacement of couch top based on clinical applications. For example, multiple couch top extensions designed and constructed for specific clinical applications may be provided. For a particular patient in a specific clinical application, a suitable couch top extension can be selected and attached to the interface plate.

Figure 3A:
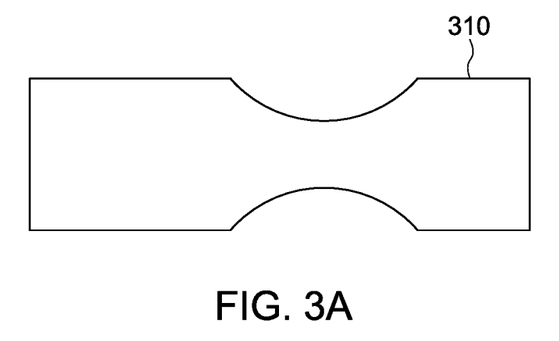
FIGS. 3A-3E depict example couch tops according to the disclosure.
Figure 3B:
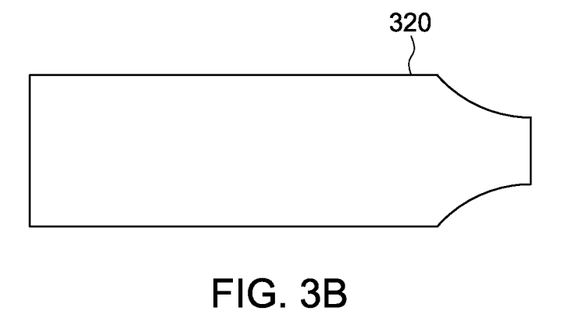
Figure 3C:
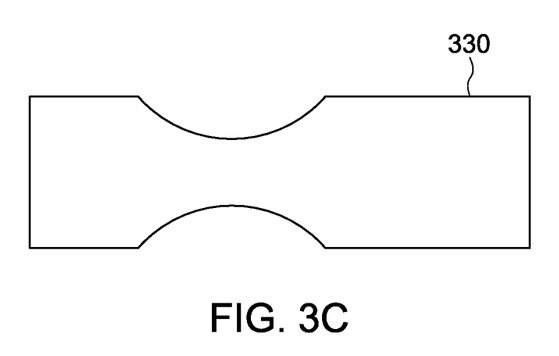
Figure 3D:
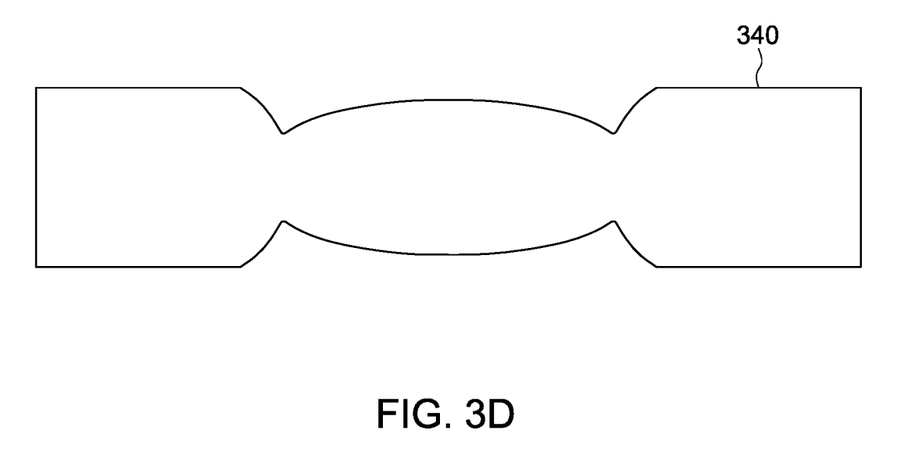
Figure 3E:
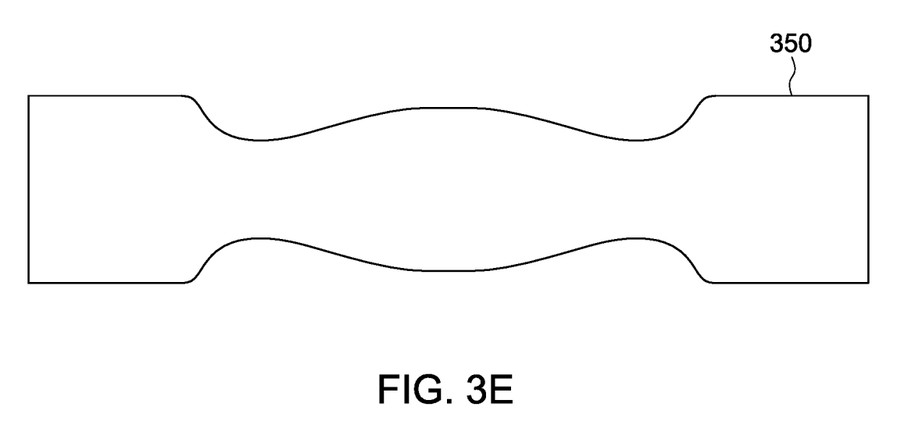

FIGS. 3A-3C depict examples of couch tops or couch top extensions according to embodiments of the disclosure. As shown, the couch tops or couch top extensions may be contoured or configured based on specific clinical applications e.g., suitable for treatment or imaging of indications in specific regions of a patient. FIG. 3A depicts an example of a couch top or couch top extension 310 configured for treatment or imaging of indications in the breast or thoracic region of a patient. As shown, the couch top or couch top extension 310 may include a lateral cutout at one or both sides. The cutout(s) allows a portion of the breast or thoracic region uncompressed, or allow radiation to be delivered to the breast or thoracic region without interference of the couch top material. FIG. 3B depicts an example of a couch top or couch top extension 320 suitable for stereotactic radiosurgery (SRS). As shown, the couch top or couch top extension 320 has a head and shoulder configuration at an end suitable for treatment or imaging of indications in the head or neck region of a patient. FIG. 3C depicts an example of a couch top or couch top extension 330 configured for treatment or imaging of indications in the abdomen or pelvic region of a patient. As shown, the couch top or couch top extension 330 may include a lateral cutout at one or both sides. The cutout(s) allows radiation to be delivered e.g., to treat prostate cancer without interference of the couch top material. In alternative embodiments, the couch top or couch top extension may be configured to have a generally rectangular supporting surface. It should be noted that the couch tops or couch top extensions 310, 320, 330 shown in FIGS. 3A-3C are provided for illustration purpose. The configuration and/or dimension of the couch tops or couch top extensions can be varied for other clinical applications or adapted for patients of different sizes. For example, a couch top or couch top extension with a smaller width and/or thickness can be constructed for a pediatric patient or for a patient of a small size and/or weight. A small width couch top or couch top extension would allow for achieving a greater yaw rotation in the bore of the radiation machine. The lateral cutout at one or both sides of a couch top or couch top extension can also be dimensioned, and/or contoured, to allow for a greater yaw rotation for a pediatric patient or for a patient of a small size. FIGS. 3D-3E show example couch tops or couch top extensions 340, 350 including a lateral cutout at one or both sides. As shown, the lateral cutouts render the width of the couch top or couch top extension 340, 350 varying along its longitudinal axis. The cutout(s) or greater cutout(s) may be located in the region(s) of the couch top or couch top extension 340, 350 that would intersect the edge(s) of the bore of the radiation machine when the couch top or couch top extension rotates about the yaw axis, thereby allowing for achieving a greater yaw rotation angle. In other words, the cutout(s) or greater cutout(s) may be located adjacent to an end or both ends of the bore of the radiation machine when the couch top supporting the patient is positioned in the bore, thereby allowing for achieving a greater yaw rotation angle. It should be noted that a couch top or couch top extension with a greater width and/or thickness can be constructed for a patient of a large size and/or weight. The use of an interface plate or a universal couch mount allows for interchanging of couch tops customized or configured for particular patients and/or clinical applications.

In another aspect of the disclosure, a radiation method is provided. The radiation method may be implemented in an O-ring type of radiation machine where a source of radiation can rotate around an opening or a bore of the radiation machine. In carrying out the radiation method, a couch top supporting a patient can be rotated about a yaw axis to place the couch top in different irradiation positions or angles, thereby allowing non-coplanar irradiation of at least a portion of the patient by the source of radiation.

Figure 4:
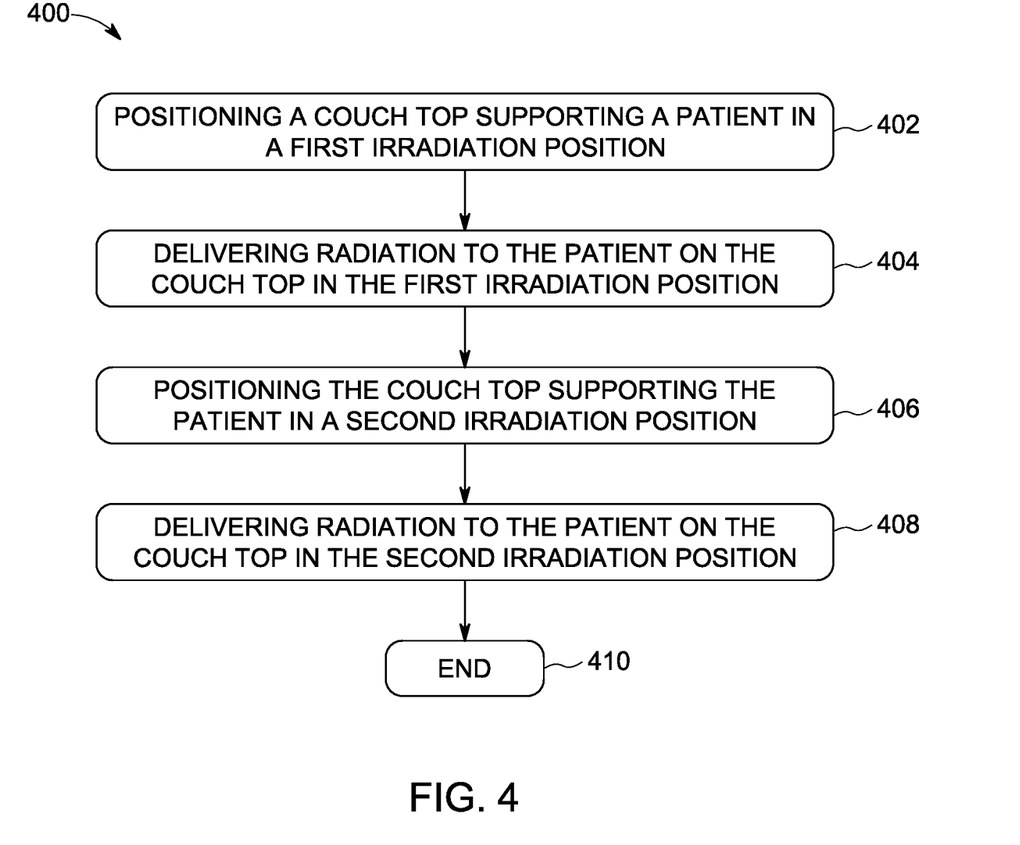
FIG. 4 is a flowchart illustrating an example radiation method according to the disclosure.

FIG. 4 is a flowchart illustrating example steps of a radiation method 400 according to the disclosure. The method 400 can be carried out in a radiation system 100 shown in FIG. 1, or a system 200 shown in FIGS. 2A-2C, or any other suitable radiation system. A suitable radiation system may include a radiation machine and a supporting device. The radiation machine may include a source of radiation and a housing defining a bore. The source of radiation may be rotatable at least partially around the bore about a rotation axis. The supporting device may include a couch top configured to position a patient or at least a portion of the patient in the bore.

With reference to FIG. 4, the method 400 may begin at step 402 where a couch top supporting a patient is positioned in a first irradiation position. This can be accomplished by extending the couch top into the bore of the radiation machine, e.g., by moving the couch and/or by moving the couple top independent of the couch. The positioning of the couch top in the first irradiation position may also involve rotating the couch top about a yaw axis, optionally about a roll axis and/or a pitch axis. In the first irradiation position, the longitudinal axis of the couch top, and thus the superior-inferior direction of the patient supported on the couch top, forms a first angle with respect to the rotation axis of the source of radiation. By way of example, the first angle may be zero degree, i.e., the longitudinal axis of the couch top and thus the superior-inferior direction of the patient supported on the couch top aligns with the rotation axis of the source of radiation. The first angle may also be non-zero degrees.

At step 404, radiation is delivered to the patient or at least a portion of the patient on the couch top in the first irradiation position. Because the source of radiation can rotate around the bore about the rotation axis, the patient or at least a portion of the patient in the first irradiation position can be irradiated by the source at multiple angles. The irradiation can be continuous while the source of radiation is swept around the patient. The irradiation can also be intermittent in a stop-and-shoot manner while the source of radiation is rotated in steps. The radiation produced by the source may be suitable for therapeutic treatment or diagnostic imaging.

At step 406, the couch top supporting the patient is positioned in a second irradiation position. This can be accomplished by rotating the couch top about a yaw axis. For example, the couch top can be rotated about a yaw axis independent of a couch. In the second irradiation position, the longitudinal axis of the couch top forms a second angle with respect to the rotation axis of the source of radiation. By way of example, the second angle may range from 5-10 degrees to 20-25 degrees. This allows the superior-inferior direction of the patient supported on the couch top to form an angle ranging from 5-10 degrees to 20-25 degrees with respect to the rotation axis of the source of radiation. The positioning of the couch top in the second irradiation position may also involve translating the couch top, and/or, rotating the couch top about a roll axis and/or a pitch axis.

At step 408, radiation is delivered to the patient or at least a portion of the patient on the couch top in the second irradiation position. Similar to step 404, because the source of radiation can rotate around the bore about the rotation axis, the patient or at least a portion of the patient in the second irradiation position can be irradiated by the source at multiple angles. The irradiation can be continuous while the source of radiation is swept around the patient. The irradiation can also be intermittent in a stop-and-shoot manner while the source of radiation is rotated in steps. According to embodiments of the disclosure, irradiation can be continuous while the couch top is moved from the first irradiation position to the second irradiation position. The operation of the source of radiation and positioning of the couch top supporting the patient can be controlled by a computer control. The method may end at step 410.

Advantageously, the radiation system and method of the disclosure combine the features of treatment efficiency, simplified collision avoidance, and self-shielding, etc. of an O-ring type of radiation system, with the flexibility of non-coplanar irradiation of a C-arm type of radiation system. As such, the performance of the radiation system can be expanded and treatment outcomes for patients can be improved.

Various embodiments of a radiation system and a radiation method have been described with reference to figures. It should be noted that the figures are intended to facilitate illustration and some figures are not necessarily drawn to scale. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. Further, the term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise. The term "coupled," "supported," "connected," "mounted", and variations are used broadly and encompass both direct and indirect couplings, supports, connections, and mounting.

Those skilled in the art will appreciate that various other modifications may be made. All these or other variations and modifications are contemplated by the inventors and within the scope of the invention.

What is claimed is:
1. A radiation system, comprising:
a radiation machine comprising a source operable to produce radiation and a housing enclosing the source, wherein the housing defines a bore and the source is rotatable at least partially around the bore; and a supporting device comprising a couch and a couch top configured to position at least a portion of a patient in the bore, wherein the couch top is rotatable about a yaw axis thereby allowing for non-coplanar irradiation of at least the portion of the patient by the source, wherein the couch top includes a couch top extension and an interface plate, and the couch top extension is removably attachable to the interface plate, allowing replacement of the couch top extension.

2. The radiation system of claim 1, wherein the couch top is rotatable about the yaw axis in at least 10 degrees.

3. The radiation system of claim 1, wherein the couch top is rotatable about the yaw axis up to 50 degrees.

4. The radiation system of claim 1, wherein the couch top is rotatable independent of the couch about the yaw axis.

5. The radiation system of claim 4, wherein the couch top is further rotatable about a pitch axis, and/or, a roll axis.

6. The radiation system of claim 5, wherein the couch top is further translatable vertically and horizontally.

7. The radiation system of claim 1, wherein the couch top extension comprises a first couch top extension having a first width dimensioned for a first patient and a second couch top extension having a second width dimensioned for a second patient, wherein the first width is different from the second width.

8. The radiation system of claim 1, wherein the couch top extension includes a cutout at a lateral side thereby providing a varying width of the couch top extension.

9. The radiation system of claim 8, wherein the cutout of the couch top extension is located at a region adjacent to an end of the bore of the radiation machine when the couch top supporting at least the portion of the patient is positioned in the bore, allowing for achieving a greater angle of rotation of the couch top about the yaw axis.

10. The radiation system of claim 1, wherein the couch top extension includes a cutout at a lateral side contoured for irradiation of a breast or thoracic region of the patient.

11. The radiation system of claim 1, wherein the couch top extension includes a head-shoulder configuration contoured for irradiation of a head or neck region of the patient.

12. The radiation system of claim 1, wherein the couch top extension includes a cutout at a lateral side contoured for irradiation of an abdomen or pelvic region of the patient.

13. The radiation system of claim 1, wherein the source is operable to produce radiation suitable for therapeutic treatment or diagnostic imaging.

14. The radiation system of claim 1, wherein the source is rotatable around the bore in at least 360 degrees.

15. A radiation method, comprising:
positioning a couch top supporting a patient in a first irradiation position in a radiation machine which comprises a source of radiation within a housing having a bore, the source of radiation being rotatable at least partially around the bore about a rotation axis, wherein in the first irradiation position, a longitudinal axis of the couch top forms a first angle with respect to the rotation axis of the source of radiation;

delivering radiation from the source of radiation to at least a portion of the patient on the couch top in the first irradiation position;

positioning the couch top supporting the patient in a second irradiation position in the radiation machine, wherein in the second irradiation position, the longitudinal axis of the couch top forms a second angle with respect to the rotation axis of the source of radiation; and delivering radiation from the source to at least the portion of the patient on the couch top in the second irradiation position, wherein
the couch top includes a couch top extension and an interface plate, and
the couch top extension is removably attachable to the interface plate, allowing replacement of the couch top extension.

16. The method of claim 15, wherein the step of positioning the couch top in the second irradiation position comprising rotating the couch top about a yaw axis.

17. The method of claim 16, wherein in the second irradiation position, the longitudinal axis of the couch top forms the second angle up to 25 degrees with respect to the rotation axis of the source of radiation.

18. The method of claim 16, wherein the step of positioning the couch top in the second irradiation position further comprising rotating the couch top about a roll axis, and/or a pitch axis.

19. The method of claim 15, wherein the source of radiation is operable to produce radiation suitable for therapeutic treatment.

* * * * *